United States Patent [19]
Cardinal et al.

[11] Patent Number: 5,345,930
[45] Date of Patent: Sep. 13, 1994

[54] METHOD AND APPARATUS FOR ASSISTING EXPULSIONAL MOVEMENT OF PULMONARY SECRETIONS VIA SUPRAMAXIMAL FLOWS

[75] Inventors: Pierre Cardinal, Gatineau; William E. Carscallen, Ottawa; Robert Ireland, Ramsay, all of Canada

[73] Assignee: National Research Council Canada Intellectual Property Services Office, Ottawa, Canada

[21] Appl. No.: 832,895

[22] Filed: Feb. 10, 1992

[51] Int. Cl.$^5$ ............ A62B 9/02; A62B 7/00; A61M 16/00; F16K 31/02
[52] U.S. Cl. ............ 128/205.24; 128/204.21; 128/204.23
[58] Field of Search ............ 128/204.18, 205.12, 128/205.19, 205.24, 207.14, 207.15, 200.24, 204.23, 204.21, 204.25; 604/35, 54, 67, 73, 118–120, 94

[56] References Cited

U.S. PATENT DOCUMENTS

| | | | |
|---|---|---|---|
| 3,923,056 | 12/1975 | Bingmann et al. | 128/204.21 |
| 3,993,059 | 11/1976 | Sjöstrand | 128/205.13 |
| 4,155,356 | 5/1979 | Venegas | 128/204.23 |
| 4,319,570 | 3/1982 | Grane | 604/35 |
| 4,448,192 | 5/1984 | Stawitcke et al. | 128/204.26 |
| 4,502,481 | 3/1985 | Christian | 128/205.24 |
| 4,795,428 | 1/1989 | Hwang | 604/73 |
| 4,973,311 | 11/1990 | Iwakoshi et al. | 604/35 |
| 4,988,336 | 1/1991 | Kohn | 604/67 |

Primary Examiner—Kimberly L. Asher
Attorney, Agent, or Firm—Juliusz Szereszewski

[57] ABSTRACT

There is described a non-invasive device designed to assist expectoration of pulmonary secretions in humans, particularly in those whose natural exhalation and natural coughing ability are impaired. The device has a valve that opens fully in not more than 10 milliseconds, a pressure sensing means generating a signal indicative of a pressure in the upper part of the subject's respiratory tract, detecting means indicating the imminent collapse of the subject's respiratory tract or a part thereof, and control means opening or closing the valve respectively in response to the signals from the sensing means and the detecting means so as to create supramaximal flows in the respiratory tract in order to stimulate the movement of secretions towards the mouth of the subject. The valve opening/closing sequence is totally subject-controlled in accordance with a method of the invention which comprises the step of inducing supramaximal flows by determining a pressure threshold for the subject to be able to effect multiple openings and closings of the valve during a single respiratory cycle, determining a subject-specified parameter indicative of a substantial collapse of the subject's respiratory tract, and having the subject exhale against the valve to effect a rapid sequence of valve opening/closing cycles which cause the supramaximal flows and resulting movement of secretions towards the mouth of the subject.

9 Claims, 3 Drawing Sheets

METHOD AND APPARATUS FOR ASSISTING EXPULSIONAL MOVEMENT OF PULMONARY SECRETIONS VIA SUPRAMAXIMAL FLOWS

FIELD OF THE INVENTION

This invention relates to a non-invasive device designed to assist expectoration of pulmonary secretions in humans whose natural exhalation and natural coughing ability are impaired.

BACKGROUND OF THE INVENTION

Physicians have long realized that patients who are unable to clear their lungs of secretions are at a much greater risk of developing pneumonia or atelectasis. These patients often die prematurely of respiratory failure. The inability to expectorate secretions is considered, by physicians, a prime contributor to the demise of patients suffering from neuromuscular disorders, cystic fibrosis, bronchiectasis, pneumonia and obstructive lung diseases. In addition, the excessive morbidity and mortality of critically ill patients requiring mechanical ventilation or patients recovering from abdominal or thoracic surgery has been attributed in part to their inability to effectively expectorate airway secretions. Patients with spinal cord injuries are also at a greater risk of respiratory failure and death because of the effect of the injury on inspiratory and/or expiratory muscles. Such patients are often unable to generate adequately high pleural pressures during coughing to achieve expectoration of secretions. Secretions that are not removed from the respiratory tract in a natural manner not only obstruct the airways thereby interfering with breathing but also become contaminated with pathogenic bacteria. This leads to an inflammatory reaction which may damage the lungs irreversibly.

As secretions can be moved from lower parts of the respiratory tract towards the upper airways (upper bronchi, trachea and mouth) by a high expiratory flow rate of air from the lungs, research work has been undertaken to induce enhanced air flow rates from the patient's lungs. Certain methods typically employ a cyclic manoeuvre in which the lungs of the patient are over pressured prior to the patient exhaling into a source of vacuum. This approach is termed "exsufflation with negative pressure" (E.W.N.P.). Note, pressures denoted negative and positive refer respectively to sub-atmospheric and super-atmospheric pressure.

As defined in Blakiston's Gould Medical Dictionary, Fourth Edition, McGraw-Hill, 1979, exsufflation means "forcible expiration; forcible expulsion of air from lungs by a mechanical apparatus", and exsufflator is defined as "an apparatus that can mimic the effect on the bronchial tree of a vigorous cough, by the sudden production of negative pressure". Urdang Dictionary of Current Medical Terms, John Viley & Sons 1981, defines exsufflation as "the forcible removal of secretions from the air passages by some form of suction apparatus". Taber's Cyclopedic Medical Dictionary, F.A. Davis Company, Edition 15, 1985, explains exsufflation as "forceful expulsion of air from a cavity by artificial means, such as use of a mechanical exsufflator". It can be seen that the definitions are not quite consistent and the term "exsufflation" has been used in the literature with certain liberty. Although having certain advantages, E.W.N.P. also has negative effects, particularly on patients with pulmonary problems. These aspects were discussed in a paper by G.J. Beck and L.A. Scarrone, Physiological effects of E.W.N.P., Diseases of The Chest, January 1956, Vol. 29, pp. 80–95. That paper describes a breathing control procedure in which the positive pressure in inspiration was built up to 40 mm Hg above atmospheric in two seconds, then a pressure drop to 40 mm Hg negative pressure would occur in 0.04 sec. The negative pressure was maintained for approximately 1.5 sec.

To improve airflow during a natural cough humans contract their expiratory muscles, raising the pleural pressure. The pleural pressure changes are not only transmitted to the alveoli, but also to the airways. Thus, if a person tries to "force" his/her expiration to achieve a relatively high air flow from their lungs, the intrathoracic pressures combined with the low static pressure within the respiratory tract resulting from the increase in expiratory flow rate tend to close, prematurely, certain parts of the respiratory tract (bronchioles, larger bronchi, trachea). The collapse of trachea and/or bronchial tubes (dynamic compression of the airways), while temporarily stopping the expiratory flow or reducing it significantly, creates a serious problem in attempting to assist the patient in breathing.

In particular, with suction applied, researchers have found that the flow of air from the lungs during the application of negative pressure (alternatively with or without positive pressure) cannot be sustained for the full lung volume, or full vital capacity (FVC); instead, the collapse of the airways or some part thereof causes discomfort of the patient. If negative pressure is still applied to the patient's respiratory tract after a partial collapse of the airways has taken place, the patient will experience an unpleasant feeling resultant from the collapse of the cheeks and/or soft palate. This sensation has been dubbed the "alligator effect". To alleviate the patient discomfort the operator must disconnect the vacuum and allow the airways to reopen and the cheeks and soft palate to move to their normal positions. This reopening of the airways and re-positioning of the cheeks and soft palate may be aided with the application of a positive pressure into the mouth. This alternation of negative/positive pressure, or negative/atmospheric pressure has so far been left to the operator's judgment, or based on average person's parameters.

Knudson, R.J. et al., Contribution of airway collapse to supramaximal expiratory flows, Journal of Applied Physiology, Vol. 36, No. 6, June 1974, describe a flowmeter to measure rapid expiratory flow events. Controlled by the patient's pleural pressure, rapid opening and closing of a valve connected with the patient's respiratory tract produced flow rate transients of short duration which exceeded the normal flow rates. The authors found that supramaximal flows generated as a result of very fast valve opening time, below 10 msec, are relatively high although of very short duration.

A Russian Author's Certificate No. 762,890 published Sep. 15, 1980 discloses a device to induce an artificial cough. The invention recognizes the fact that the displacement of secretions from the lower parts of the respiratory tract to the upper parts—bronchi, trachea, mouth—is promoted by a fast flow of air from the lungs during exhalation. The device comprises a mask, a vacuum volume connected to a membrane switching mechanism having an inlet valve connected to a rarefaction source, and an outlet valve connected to the mask. The switching mechanism consists of three membranes and a nozzle. A coughing impulse is created by connecting the rarefaction source with the lungs. The specification is silent on the timing of the alternating vacuum phases.

While the above-described proposals are useful in removing secretions from the respiratory tract, they do not fully solve the problem of expectoration of secretions in weakened individuals without causing their discomfort.

SUMMARY OF THE INVENTION

It is an object of the present invention to provide an apparatus for inducing the movement of mucus, phlegm, and other secretions from the lower portions to upper portions of the patient's respiratory tract (mouth ward) thereby facilitating the removal of these secretions from the body.

According to the invention, a device is provided which comprises a quick-acting valve having an inlet adapted to be connected to the upper part of a subject's respiratory tract, the valve openable in a time not exceeding 10 milliseconds, and preferably closable in a time not exceeding 10 milliseconds. The device further comprises pressure sensing means adapted to generate a signal indicative of the pressure in the upper part of the respiratory tract, detecting means adapted to generate a signal indicative of a collapse of at least a part of the respiratory tract, first control means operative to open the valve in response to the signal from said pressure sensing means indicating that the pressure in the upper respiratory tract (upper airways) reaches or exceeds a predetermined level, and second control means operative to close the valve in response to a signal from the detecting means when the respiratory tract substantially collapses as a result of the expiration.

Specifically, the second control means may be operative to close the valve after a predetermined, subject-specific period of time. This subject-specific period of time is not longer than the period of time in which a substantial collapse of the subject's airways has occurred as a result of applying negative pressure to the upper part of the respiratory tract. Alternatively, the second control means may be operative to close the valve upon indication that the expiratory flow rate has been significantly reduced from its initial value, or upon an indication that the pressure in the upper respiratory tract has dropped, to a degree that has resulted in a substantial collapse of the airways.

In another aspect of the invention, there is provided a method of assisting exsufflation, which comprises:

a) determining a pressure threshold which a subject is comfortably capable of reaching or exceeding in his/her upper respiratory tract through the expiratory cycle.

b) determining at least one subject-specific parameter indicative of the subject's respiratory tract collapse upon forced expiration to a degree where the respiratory flow is substantially stopped or obstructed.

c) having a subject inhale freely and then exhale against an apparatus having an initially closed quick-acting valve which is adapted to open upon the pressure in the upper respiratory tract reaching the pressure threshold and to close in response to the collapse-indicative parameter being met, the pressure threshold being such that the subject is capable of effecting multiple opening and closing of the valve during a single expiratory cycle.

The method of the invention, as used in conjunction with the apparatus, is effective in generating an expansion wave in the subject's respiratory tract. The wave, which travels at the speed of sound from the mouth down the trachea to the small distal airways, brings about a high-velocity air flow generated behind the wave. The velocity, in the order of 75 ft/sec (22.5 m/sec) causes a substantial part of the secretions to move from the small airways to the larger airways (bronchioles, bronchi, trachea).

The apparatus of the invention is associated, preferably, with a source of negative pressure to promote the generation of the expansion wave. It is known that the pleural pressure which a subject generates to exhale, acts to cause dynamic compression of the airways, leading to a partial collapse thereof, if the expiratory flow exceeds a certain level, i.e. if the subject tries to exhale "as strongly as possible" for an extended period of time. The invention accounts for the fact that the acceleration of expiratory flow by means of negative pressure involves a correspondingly faster occurrence of the airway collapse. The dependence of the valve opening/closing cycle on the pressure in the upper airways (rather than on the pleural pressure which does not vary drastically during the use of the apparatus of the invention) and on the airway collapse condition respectively is believed to be the important feature of the present invention. The design of the apparatus makes it possible to generate a number of above-discussed expansion waves during one expiratory cycle, each wave being generated, substantially, when the airways are open.

BRIEF DESCRIPTION OF THE DRAWINGS

The invention will be explained in more detail in conjunction with the following drawings.

DETAILED DESCRIPTION OF PREFERRED EMBODIMENTS

Figure 1:
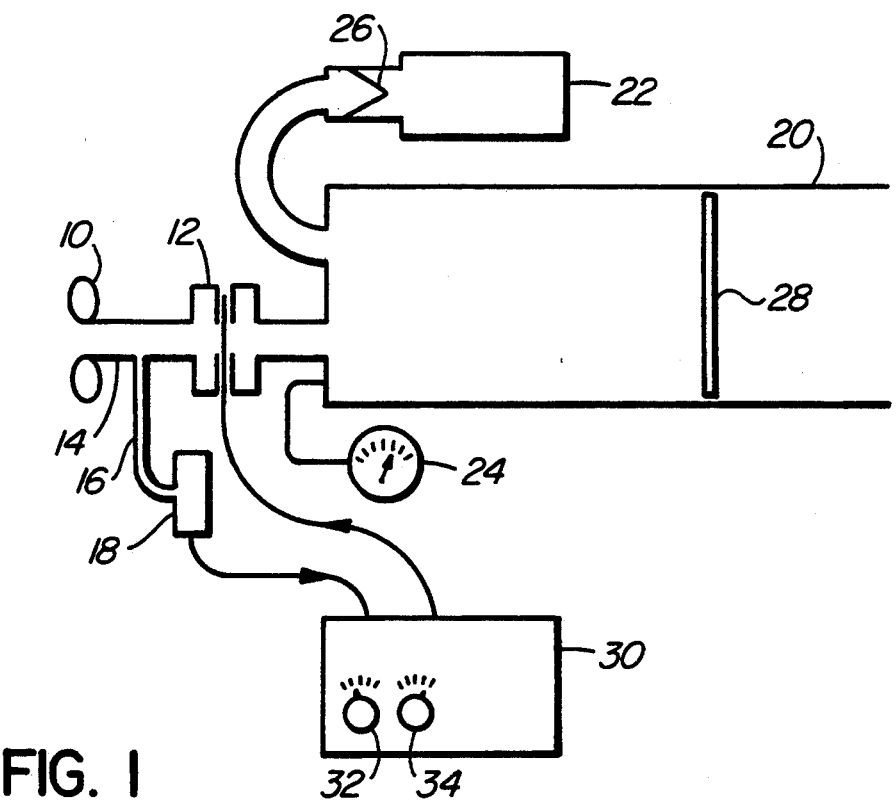
FIG. 1 is a schematic representation of one embodiment of the apparatus of the invention including a negative pressure attachment.

According to a first embodiment of the invention as illustrated in FIG. 1, the apparatus of the invention comprises a face mask 10 which is adapted to seal the face of the patient, the mask being connected to a quick-acting valve 12 via a rigid tubing 14 which has a pressure port 16. The port 16 is in turn connected to a transducer 18 which converts the pressure at the port into an electric voltage signal.

The outlet of the valve 12 is connected via another rigid tubing to a vacuum cylinder 20 which is connected via a one way valve 26 to a vacuum pump 22 and has a vacuum gauge 24. The volume of the vacuum cylinder can be adjusted by means of a piston 28.

The output of transducer 18 (which relates to upper airway pressure) is connected to electronic control means 30 which processes the signal from transducer 18 and compares it to a pressure set point which is predetermined by way of set point means 32. If the pressure is above the pressure set point the valve 12 is opened. The length of time that valve 12 stays open is determined by time set point means 34. When valve 12 is opened the upper airway pressure measured at port 16 will decrease. When valve 12 is closed the pressure in the upper airways starts to increase and when the pressure again reaches the pressure of set point 32 the valve 12 opens for the time determined by time set point means 34. These events continue until the patient no longer exerts positive pressure associated with exhaling.

Figure 3:
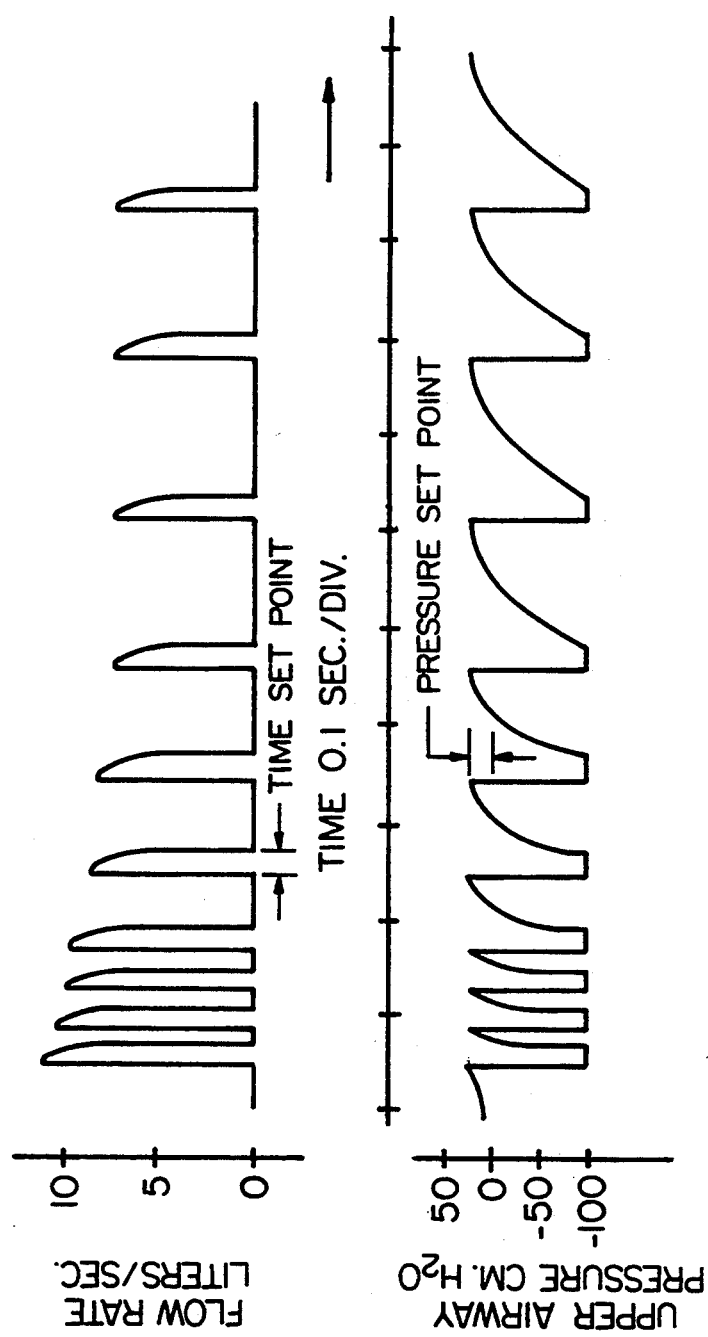
FIG. 3 is a graph showing flow rate and upper airway pressure vs time for the first embodiment of the apparatus at constant vacuum.

Constant vacuum can be maintained in the vacuum cylinder 20 by allowing a vacuum pump 22 of sufficient capacity to run continuously. The results of this condition of constant vacuum is illustrated in FIG. 3 showing the flow rate and the upper airway pressure in relation to time for a typical patient with obstructive lung disease.

Figure 4:
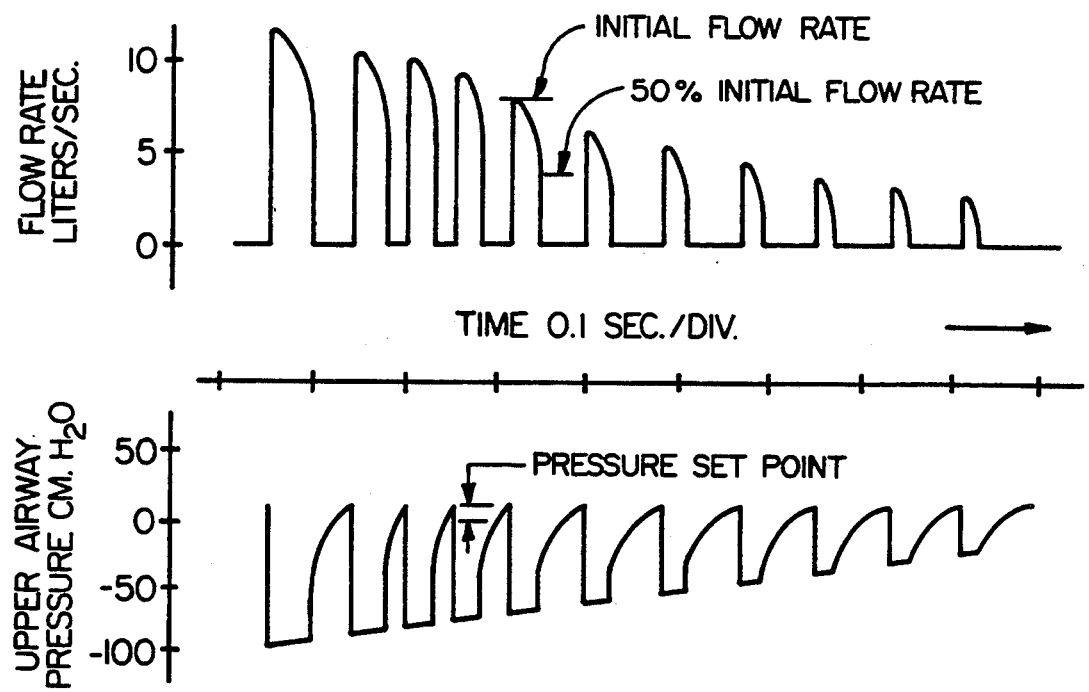
FIG. 4 is a graph showing flow rate and upper airway pressure vs time for the second embodiment of the apparatus with fixed volume vacuum source.

If the vacuum pump 22 is switched off, the vacuum in cylinder 20 will decrease as the patient exhales. This degree of decrease can be controlled by adjusting the position of piston 28. The result of this condition of constant volume is illustrated in FIG. 4 showing the rate of flow and upper airway pressure in relation to time again for a typical patient with obstructive disease. Note that in this case, unlike FIG. 3 both the air flow and the upper airway pressure lessen as the patient exhales.

In the first embodiment, the time set point means 34 is the collapse-detecting means. The pressure set point means 32 and a part of the control means 30 function as the first control means; and another part of the control means 30, responsive to the time set point means 34, functions as the second control means operative to close the valve 12.

Figure 2:
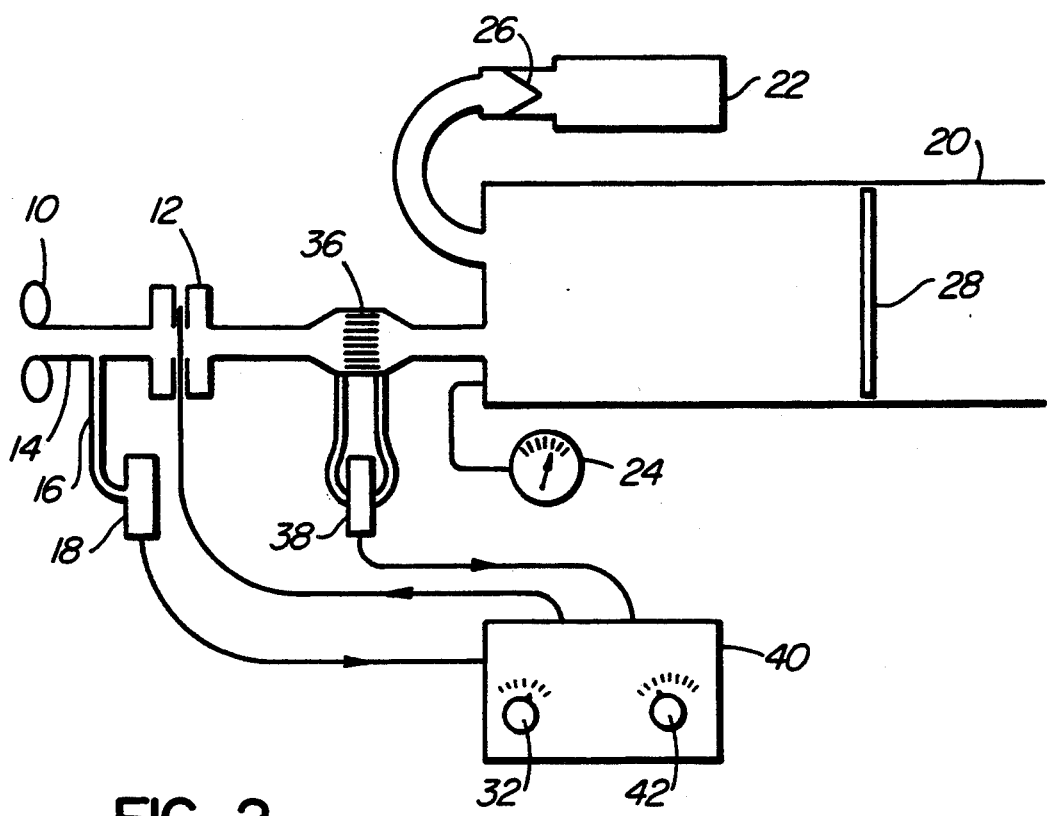
FIG. 2 is a schematic representation of a second embodiment of the apparatus of the invention including a negative pressure attachment.

In a second embodiment illustrated in FIG. 2 in which like reference numerals denote similar elements as in FIG. 1, the outlet of valve 12 is connected to a pneumotach 36, i.e. a flow measuring element which converts air flow rate into a pressure differential signal. The signal is then converted by a transducer 38 into a electrical voltage signal.

The output of transducer 18 (which relates to upper airway pressure) is connected to electronic control means 40 which processes the signal from transducer 18 and compares it to pressure set point means 32, If the pressure is above the pressure set point 32, the valve 12 is opened. When valve 12 is opened the upper airway pressure will decrease rapidly, and the flow rate will (initially) increase rapidly to a peak value and then tend to subside. When the flow rate subsides to a value less then a set percentage (the percentage being set by percentage set-point means 42) of this peak value, then valve 12 is closed. When valve 12 is closed the flow rate drops to zero and the pressure in the upper airways starts to increase. When the upper airway pressure again reaches the pressure of set point 32, the valve 12 opens again until the flow rate falls below a set percentage of its peak value. These events continue until the patient no longer exerts positive pressure associated with exhaling.

In the second embodiment, the pneumotach 36 is the collapse-detecting means. The pressure set point means 32 and a part of the control means 40 function as the first control means; and the percentage set-point means 42 and another part of the control means 40 function as the second control means operative to close the valve 12.

All the elements described above are available on the market. It is important that the valve is of a design enabling its opening and closing in a short period of time. As indicated by previous workers, it is advantageous that the opening time of the valve is not more than 10 milliseconds. Preferably, the closing of the valve should also take approximately the same time. The fast opening of the valve creates the desired supramaximal expiratory flow, while fast closing prohibits the "alligator effect".

A quick acting valve suitable for the purposes of the present invention is described for example in Journal of Applied Physiology, Volume 147, 1959, pg. 40.

While the embodiments of the invention described above and illustrated in FIG. 1 and FIG. 2 comprise a source of reduced pressure, it has been found that the apparatus is effective in creating the cyclic supramaximal expiratory flows, aiding the expectoration of secretions, also without the stimulation by means of negative pressure. The latter, however, enhances the action of the apparatus.

FIG. 3 illustrates the sequence of events of the first embodiment with a constant vacuum source. FIG. 3 shows two graphs. The ordinate of the upper graph is the flow rate of air from the mouth of the patient while the ordinate of the lower graph is the patient's upper airway pressure. The abscissa for both graphs is time. Noteworthy are the fluctuations in both flow rate and upper airway pressure as the valve 12 opens and closes. Valve 12 opens when the patient's upper airway pressure reaches the pressure set point 32 and closes after a time duration established by the time set point 34. The closing of valve 12 terminates the patients exhalation of air and causes the flow rate to drop to zero. As the process of the patients exhalation is not over the upper airway pressure starts to increase until it once again reaches the pressure set point 32 at which point in time valve 12 reopens for the previously describe time duration. This sequence continues until the patient can no longer generate the positive pressure required by set point 32 to trigger the opening of valve 12.

FIG. 4 illustrates the sequence of events of the second embodiment with a constant volume vacuum source. FIG. 4 shows two graphs. The ordinate of the upper graph is the flow rate of air from the mouth of the patient while the ordinate of the lower graph is the patient's upper airway pressure. The abscissa for both graphs is time. Noteworthy, are the fluctuations in the flow rate at the mouth of the patient and in upper airway pressure as a function of time. These fluctuations are controlled by and correlated to the opening and closing of valve 12. Valve 12 opens when the upper airway pressure reaches the pressure set point 32. Valve 12 then remains open until the flow rate of air being exhaled by the patient drops to 50 percent of the peak value. At this point in time valve 12 closes. The closing of valve 12 terminates the patients exhalation of air and causes the flow rate to drop to zero. As the process of the patients exhalation is not over the upper airway pressure starts to increase until it once again reaches the pressure set point 32 at which point in time valve 12 reopens. This sequence continues until the patient can no longer generate the positive pressure required by set point 32 to trigger the opening of valve 12.

Figure 5:
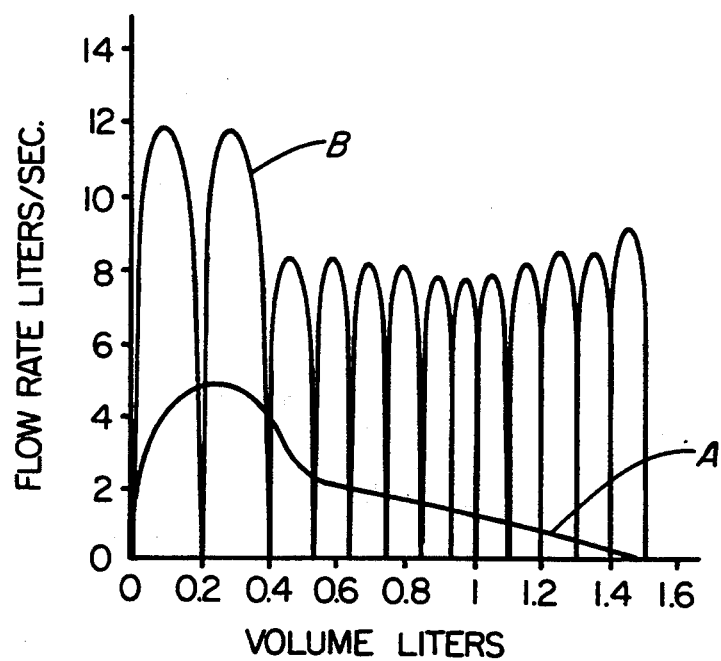
FIG. 5 is a graph showing flow rate vs volume expelled for a patient with obstructive lung disease: A) without assistance and B) with use of the apparatus of the invention.

FIG. 5 illustrates the patient's exhaled flow rate vs volume for a typical unassisted patient with restrictive lung disease, trace "A" and with assistance of the invention, trace "B". The ordinate of the graph is the flow rate of air from the mouth of the patient. The abscissa is time. Noteworthy are the supramaximal flow rates achieved with use of the invention. These supramaximal flow rates enhance removal of secretions from the patient's distal and upper airways.

A METHOD OF USING THE FIRST EMBODIMENT

A method of use of the apparatus of the invention will now be described in more detail. A patient is evaluated first to determine a pressure threshold at which valve 12 will open in the actual exsufflation procedure. To this end, the patient is requested to breathe out repeatedly at various threshold pressures and to select the optimal pressure which will minimize both patient expiratory effort and upper airway discomfort yet causing valve 12 to open.

In a subsequent step, a parameter indicative of a substantial collapse of the patient's respiratory tract is determined. This can be effected by measuring the time period between the opening of the valve and the moment the flow rate decreases to approximately 50% of initial value or when the patient upon forced expiration (i.e. with the use of negative pressure) starts to experience discomfort as a result of either or both upper airway and soft palate collapsing. The second control means of the apparatus is then adjusted accordingly to effect the closing of the valve, following its opening, within a time interval not exceeding the above-defined period of time. Predetermined temporal variations of expiratory flow rates may be used for this purpose.

After the pressure threshold and the collapse-indicating parameter have been predetermined and the first and second control means of the apparatus adjusted accordingly, the patient is instructed to breathe against the initially closed valve through the face mask. The vacuum cylinder 20 is used optionally. In the fixed volume version, the vacuum level and the volume of the cylinder are preset such that the total volume the cylinder can "suck in" or the patient can exhale before the pressure in the cylinder reaches atmospheric, does not exceed the sum of the subject's tidal lung volume and expiratory reserve lung volume.

As the patient exhales against the valve, the valve opens and closes rapidly. The patient inhales air from outside the apparatus and exhales against the valve again. The patient continues this process until he/she feels secretions being moved from the lower parts of the respiratory tract towards the upper airways (upper bronchi, trachea and mouth). The patient expectorates these secretions by coughing. The duration of this procedure is nominally the length of time spent undergoing regular physiotherapy but it may be lengthened or shortened to suit the patient. Typically, the time is lengthened as there is minimal patient fatigue and discomfort associated with this procedure.

A METHOD OF USING THE SECOND EMBODIMENT

The pressure threshold (pressure set point means 32) is determined in a way similar to that as described in the "a method of using the first embodiment".

In the situations where the vacuum cylinder 20 will be employed: in the fixed volume version, the vacuum level and the volume will be determined (preset) as described in the "method of using the first embodiment". In the constant vacuum version the vacuum should be set to approximately 100 cm. $H_2O$ and altered later as may be required.

The second embodiment employs a percentage set point means 42. which typically will be set initially to a value of approximately 90%. The patient will start to use the equipment, exhaling into it as described previously. The percentage set point will then be lowered by 5% each successive exhalation cycle (under the supervision of medical personnel) until a degree of discomfort is felt, then increased slightly to relieve discomfort. The percentage set point would then be left in this position for the remainder of session. It may be found that by varying both the percentage set point and/or the vacuum level and/or the vacuum volume it may be possible in specific patients to move secretions from different airway regions of the lungs.

Again as above (a method of using the first embodiment) the patient continues this process until he/she feels secretions being moved from the lower parts of the respiratory tract towards the upper airways and expectorates these secretions by coughing.

We claim:

1. An apparatus for assisting the movement of pulmonary secretions towards the outlet of a subject's respiratory tract by inducing supramaximal flows in a subject's respiratory tract during the subject's exhalation, the apparatus comprising means for moving the secretions toward the outlet of the subject's respiratory tract, said means including:
    a) a valve having an opening time to a fully opened condition of not more than 10 milliseconds against a unidirectional expiratory flow of the subject, the valve having an inlet and an outlet, the inlet being adapted to be connected to the outlet of the respiratory tract of the subject;
    b) pressure sensing means for generating a first signal indicative of a positive pressure in the upper part of the respiratory tract;
    c) means for generating a second signal corresponding to a substantial collapse or near-collapse of the respiratory tract;
    d) valve opening control means including means for establishing a predetermined pressure level and operative to open the valve in response to said first signal from said pressure sensing means indicating that the sensed pressure reaches or exceeds said predetermined level; and
    e) valve closing control means operative to close the valve in response to said second signal corresponding to a substantial collapse or near-collapse of the respiratory tract, said opening of said valve inducing a cycle of events in the respiratory tract including a supramaximal expiratory flow and a resulting near-collapse of said tract followed by a closing of said valve, said cycle having a duration considerably shorter than an exhalation time of the subject, said valve opening and valve closing control means being operative, synchronously with said cycle, to repetitively open and close said valve a plurality of times during a single exhalation of the subject, said repetitive opening and closing of said valve thus creating a series of said supramaximal flows which is effective to move secretions towards the outlet of the subject's respiratory tract.

2. The apparatus according to claim 1, further comprising a source of controlled reduced pressure, connected to the outlet of the valve.

3. The apparatus according to claim 2, where the source of reduced pressure is a fixed volume/variable pressure chamber.

4. The apparatus according to claim 3 wherein said fixed volume/variable pressure chamber has a preset volume and vacuum level selected so that a maximum volume of gas drawn by the chamber does not exceed the sum of the subject's tidal lung volume and expiratory reserve lung volume.

5. The apparatus according to claim 2, wherein the source of reduced pressure is a substantially uniform vacuum source.

6. A method of assisting the movement of pulmonary secretions towards the outlet of a subject's respiratory tract by inducing supramaximal flows in the respiratory tract, comprising the steps of:

a) determining a pressure threshold which the subject is comfortably capable of reaching in the respiratory tract through an expiratory cycle when breathing against an initially closed valve which opens upon the pressure in the upper respiratory tract reaching the pressure threshold;

b) determining a subject-specific parameter indicative of a substantial collapse of the subject's respiratory tract to a degree where the respiratory flow is substantially stopped or obstructed for closing the valve when the parameter is reached during the expiratory cycle;

c) choosing a valve opening pressure threshold and a valve closing parameter for operation of the valve wherein the subject can effect multiple openings and closings of said valve during a single expiratory cycle; and d) having a subject repeatedly inhale freely and then exhale against an initially closed valve which opens in not more than 10 milliseconds upon the pressure in the upper respiratory tract reaching the chosen pressure threshold and closes in response to the chosen valve closing parameter being met, the opening and closing of said valve generating supramaximal flows in the respiratory tract of the subject, said flows being effective to move pulmonary secretions towards the outlet of the subject's respiratory tract.

7. The method according to claim 6 wherein the parameter is selected to correspond to a period of time in which at least a part of the subject's respiratory tract collapses upon forced expiration thereby substantially obstructing the expiratory flow.

8. The method according to claim 6 wherein the parameter is selected to correspond to the expiratory flow rate.

9. The method according to claim 6 wherein the duration of full closure of the valve is selected to be not more than 10 milliseconds.

* * * * *